United States Patent
Weinberg et al.

(10) Patent No.: US 8,490,504 B2
(45) Date of Patent: Jul. 23, 2013

(54) FATIGUE EVALUATION OF PROSTHESES BY RADIAL EXCITATION OF TUBULAR STRUCTURES

(75) Inventors: Craig Weinberg, Denver, CO (US); Benjamin McCloskey, Evergreen, CO (US); Steven Weinberg, League City, TX (US)

(73) Assignee: Biomedical Device Consultants and Laboratories of Colorado, LLC, Wheatridge, CO (US)

( * ) Notice: Subject to any disclaimer, the term of this patent is extended or adjusted under 35 U.S.C. 154(b) by 293 days.

(21) Appl. No.: 12/975,772

(22) Filed: Dec. 22, 2010

(65) Prior Publication Data

US 2011/0146385 A1 Jun. 23, 2011

Related U.S. Application Data

(60) Provisional application No. 61/289,135, filed on Dec. 22, 2009.

(51) Int. Cl.
*G01N 3/36* (2006.01)

(52) U.S. Cl.
USPC ............... 73/865.6; 73/760; 73/788; 73/856; 73/866

(58) Field of Classification Search
USPC ................. 73/37, 760, 788, 856, 865.6, 866
See application file for complete search history.

(56) References Cited

U.S. PATENT DOCUMENTS

| | | | |
|---|---|---|---|
| 3,911,735 A * | 10/1975 | Di Crispino | 73/841 |
| 4,381,663 A | 5/1983 | Swanson | |
| 4,972,721 A | 11/1990 | Conti | |
| 5,272,909 A * | 12/1993 | Nguyen et al. | 73/37 |
| 5,406,857 A * | 4/1995 | Eberhardt et al. | 73/866.4 |
| 5,528,944 A * | 6/1996 | Hoyt et al. | 73/866.4 |
| 5,670,708 A | 9/1997 | Vilendrer | |
| 5,792,603 A * | 8/1998 | Dunkelman et al. | 435/1.2 |
| 6,062,075 A * | 5/2000 | Ritz et al. | 73/168 |
| 6,810,751 B2 * | 11/2004 | Moreno et al. | 73/849 |
| 6,881,224 B2 * | 4/2005 | Kruse et al. | 623/2.11 |
| 7,254,988 B2 * | 8/2007 | Keeble | 73/37 |
| 7,348,175 B2 * | 3/2008 | Vilendrer et al. | 435/284.1 |
| 7,363,821 B2 * | 4/2008 | Black et al. | 73/810 |
| 7,472,604 B2 * | 1/2009 | Moore et al. | 73/849 |
| 7,587,949 B2 * | 9/2009 | Dingmann et al. | 73/863.02 |
| 7,621,192 B2 * | 11/2009 | Conti et al. | 73/865.6 |
| 8,034,608 B2 * | 10/2011 | Dancu | 435/284.1 |

(Continued)

OTHER PUBLICATIONS

International Search Report and Written Opinion dated Sep. 9, 2011, PCT/US2010/061740, 9 pages.

*Primary Examiner* — David Rogers
(74) *Attorney, Agent, or Firm* — Dorsey and Whitney LLP

(57) ABSTRACT

Prostheses are fatigue tested using an apparatus under simulated physiological loading conditions. A fluid housing defines an entrance chamber having fluid outflow ports and an exit chamber having opposing fluid inflow ports and a central flow conduit in communication with the entrance chamber and the exit chamber. A plurality of housing tubes into which prosthesis are deployed may extend between the fluid outflow and inflow ports. Alternatively, tubular prostheses may be connected directly between the inflow and outflow ports. A reciprocating linear drive pump having a flexible diaphragm is provided to cyclically pressurize fluid through a common closed loop within the fluid housing and drive the pressurized fluid through the prosthesis being tested. The test system is capable of rotation independent of the motor drive for accurate diameter measurements of all test samples at elevated frequencies.

33 Claims, 9 Drawing Sheets

U.S. PATENT DOCUMENTS

| | | | |
|---|---|---|---|
| 8,196,478 B2 * | 6/2012 | Lorenz et al. | 73/856 |
| 8,318,414 B2 * | 11/2012 | Dancu et al. | 435/1.2 |
| 2003/0066338 A1 * | 4/2003 | Michalsky et al. | 73/37 |
| 2003/0110830 A1 * | 6/2003 | Dehdashtian et al. | 73/37 |
| 2003/0125804 A1 | 7/2003 | Kruse et al. | |
| 2003/0199083 A1 * | 10/2003 | Vilendrer et al. | 435/297.2 |
| 2004/0016301 A1 | 1/2004 | Moreno et al. | |
| 2010/0225478 A1 * | 9/2010 | McCloskey et al. | 340/540 |
| 2011/0259439 A1 * | 10/2011 | Neerincx | 137/223 |

* cited by examiner

FATIGUE EVALUATION OF PROSTHESES BY RADIAL EXCITATION OF TUBULAR STRUCTURES

CROSS REFERENCE TO RELATED APPLICATIONS

This application claims the benefit of priority pursuant to 35 U.S.C. §119(e) of U.S. provisional application No. 61/289,135 filed 22 Dec. 2009 entitled "Fatigue evaluation of prostheses by radial excitation of tubular structures," which is hereby incorporated herein by reference in its entirety.

TECHNICAL FIELD

This disclosure concerns fatigue testing of prosthetic devices, e.g., prosthetic stents, grafts, stent-grafts, and other prosthesis (collectively referred to hereinafter as "prostheses"), under simulated physiological loading conditions and high-cycle applications.

BACKGROUND

The Food & Drug Administration (FDA) and other worldwide regulatory agencies require medical device manufacturers to submit clinical and in vitro test data before commercial approval of prosthetic devices. As a part of this action, these devices are typically tested to 400,000,000 cycles simulating 10 years of life in the human body at an average heart rate of 80 beats per minute. Prosthetic testing apparatus and methods, such as those outlined by Vilendrer in U.S. Pat. No. 5,670,708 and Conti in U.S. Pat. No. 4,972,721, require significant capital investment and, in the case of the system outlined in U.S. Pat. No. 4,972,721, offer limited operating frequencies and measurement capabilities. Additionally, these test systems are typically built to order based on specific target prosthetic device sizes and configurations, limiting testing flexibility. Furthermore, current systems employ a flexible metallic bellows or conventional piston and cylinder as drive members to provide the pressure actuation.

These traditional fluid drive technologies have several shortcomings. For example, flexible metallic bellows are not ideal because they require high forces to operate and resonate at specific frequencies, necessitating the use of larger driving systems and limiting the available test speeds. Also, piston and cylinder arrangements employ traditional seals which are subject to friction and thus have severely limited life in high cycle applications. Additionally, known single drive systems create standing waves along the length of the prosthetic devices being tested, which is not a natural pressure waveform found in the human body. Therefore, the test sample is not excited in a clinically relevant manner.

The information included in this Background section of the specification, including any references cited herein and any description or discussion thereof, is included for technical reference purposes only and is not to be regarded subject matter by which the scope of the claimed invention is to be bound.

SUMMARY

Implementations of fatigue testing systems and devices herein simulate physiologic loading conditions on prosthetic devices at elevated testing frequencies. Generally, fatigue testing is accomplished by first deploying the prosthesis in an appropriately sized flexible housing tube or other appropriate structure. The housing tube with the prosthesis being tested are then subjected to physiologically appropriate conditions, which may include, but are not limited to, pressure, radial strain, temperature, and flow. Testing and test conditions are controlled by a computer that permits both input of test conditions and monitors feedback of the test conditions during testing. System control may be either an open loop paradigm that requires user intervention in the event a condition falls outside specified condition parameters or a closed loop model in which the system monitors and actively controls testing outputs in order to ensure that the testing parameters remain within specified conditions.

A working fluid, which may be water, saline, a saline/glycerin solution, a glycerin/water solution, or a blood analog or substitute, is employed within the testing system. The working fluid may be selected to simulate one or more attributes of human blood, such as density, viscosity, or temperature. For example, in certain instances, physiological saline which does not simulate the viscosity of blood, but simulates density, may be used. In other cases a saline/glycerin solution may be employed to simulate blood density and viscosity.

Plural prosthesis housing tubes, or the prostheses themselves, are coupled in parallel to a main housing having plural fluid distribution channels in communication with each of the housing tubes or prostheses. The main housing consists generally of a single fluid reservoir in fluid flow communication with each of the prosthesis housing tubes or prosthesis itself. The single fluid reservoir includes an entrance section and an exit section in fluid communication via a central flow conduit. The entrance section includes a plurality of fluid outlet ports, a single fluid flow inlet port and single fluid port in communication with the central flow conduit. The exit section includes a plurality of fluid outlet ports, a single fluid flow outlet port and single fluid port in communication with the central flow conduit. An external fluid reservoir provides a fluid draw source for the circulation pump and maintains the working fluid at the specified temperature.

Implementations of fatigue testing devices generally include a linear motor coupled with a fluid drive member. The fluid drive member impinges upon the entrance section of the fluid reservoir to provide a motive force to drive the working fluid through its cycles within the main housing and the housing tubes. In one implementation, the fluid drive member is coupled to an opening in the entrance chamber and is reciprocally moveable to pressurize and depressurize fluid within the entrance housing. The fluid drive member is a flexible diaphragm which is highly compliant with low resistance to axial deformation across its entire axial range of motion.

These components operate together to act as a fluid pump and when combined with the fluid control system, provide the pressure, flow, and temperature environment necessary to cycle the prosthesis under physiologic conditions. The internal conditions, which include, among other things, temperature and pressure, are electrically communicated to monitoring and controlling software on a test system computer. The external tube housing diameter or prosthesis is directly monitored through an optical micrometer system, consisting of a LED or laser-based, high-accuracy, optical micrometer, paired with a precise liner positioning system. The main housing may rotate about the system central axis allowing individual tube measurements at all test locations. The dynamics of the fluid pump and, therefore, the system dynamics are controlled via test system control software. The pressure field resulting from the pump motion is easily adjusted and controlled. All system inputs and outputs may be continuously monitored and directed into a software-based control and alarm system, allowing the system to automatically adjust and halt if any signal deviates outside of the specified test conditions.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of this technology is provided in the following written description of various embodiments, illustrated in the accompanying drawings, and defined in the appended claims to the invention.

BRIEF DESCRIPTION OF THE DRAWINGS

Various features and functions of the disclosed technology may be better understood when considered in conjunction with the accompanying drawings, in which like reference characters designate the same or similar parts throughout the several views.

DETAILED DESCRIPTION

Figure 1:
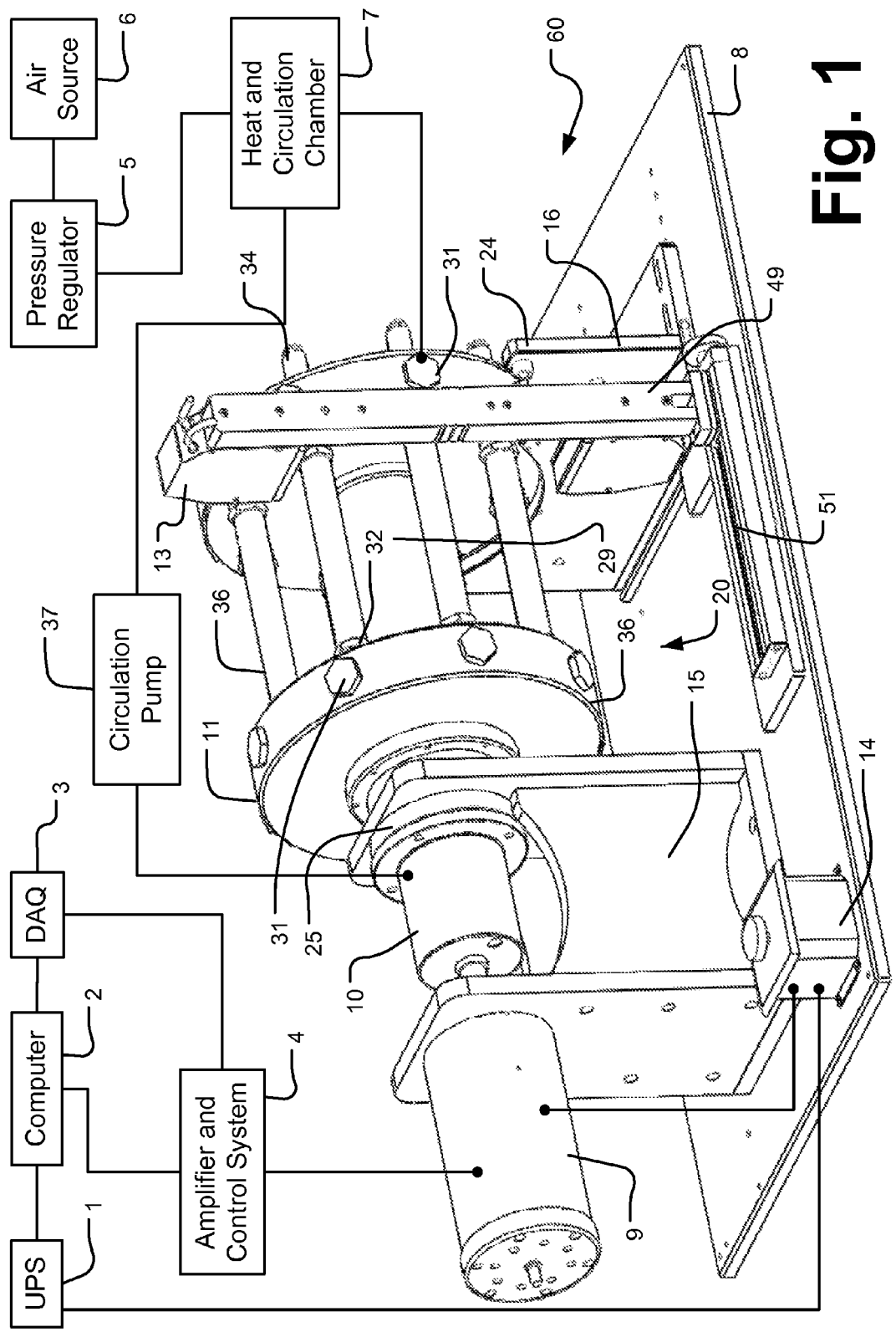
FIG. 1 is a combination block diagram and isometric view illustrating a main testing apparatus and related control systems of an implementation of a fatigue-testing system for prostheses.
Figure 2:
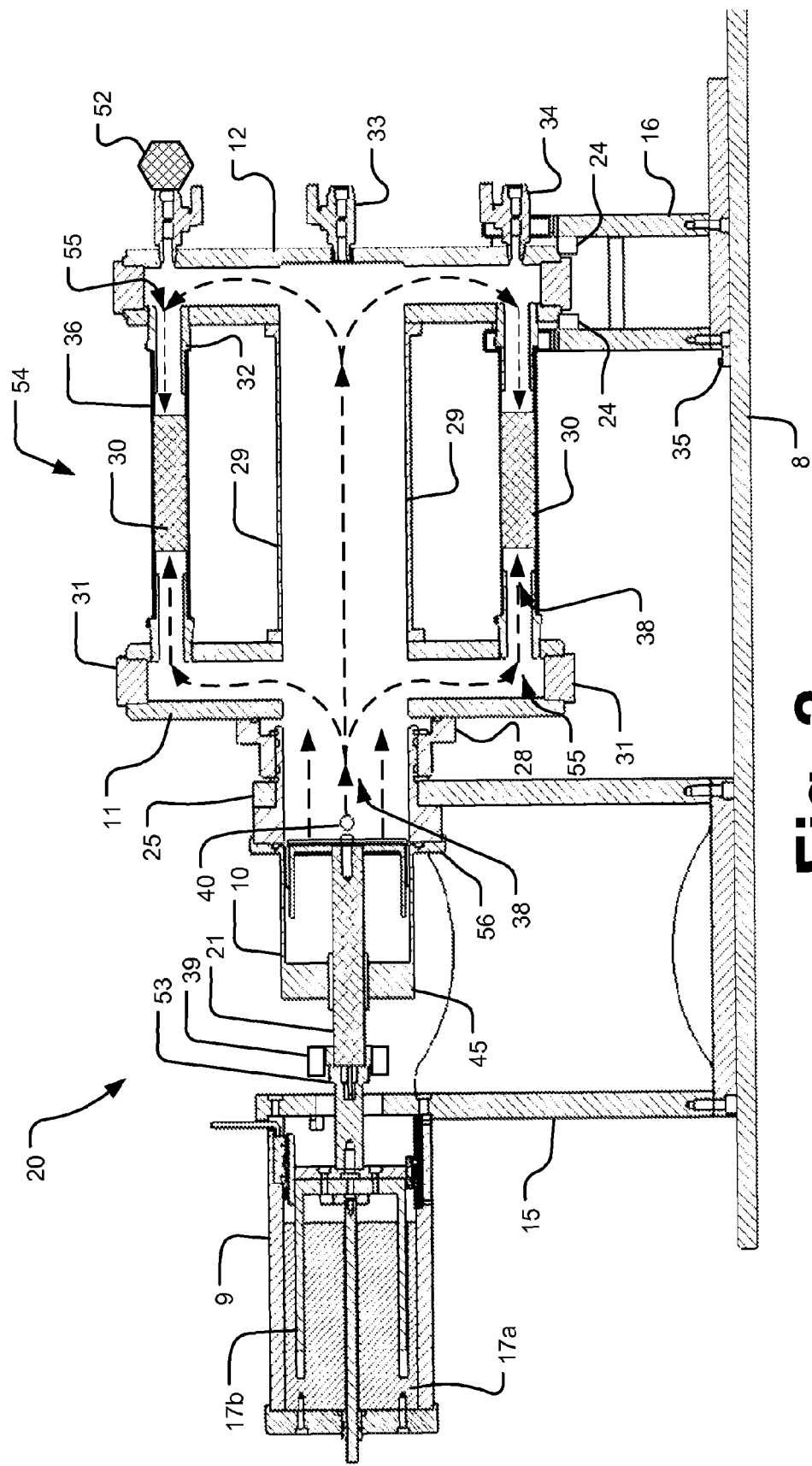
FIG. 2 is a cross-section view of the fatigue-testing apparatus of FIG. 1 showing the internal fluid chamber coupled with the linear drive system.

FIGS. 1 and 2 depict a fatigue-testing system 60 having a fatigue-testing device 20 operably connected to a data acquisition (DAQ) device 3 and to an amplifier and control system 4. These components are, in turn, operably connected to a microprocessor-based computer 2. All systems are preferably connected to an uninterrupted power supply (UPS) 1. The fatigue testing device 20 is composed of a pressurizable fluid housing 54 formed as a disk-shaped manifold or entrance chamber 11 and a disk-shaped manifold or exit chamber 12 connected by a cylindrical central flow conduit 29. The entrance and exit chambers 11, 12 are supported, respectively, by an entrance support structure 15 and an exit support structure 16. The support structures 15, 16 are affixed to a base plate 8.

A plurality of flexible tubes 36, or other prosthesis-housing structures, or the prostheses themselves, extend between and are in fluid communication with the entrance chamber 11 and the exit chamber 12. The tubes 36 are parallel to and arranged circumferentially around and spaced apart from the central flow conduit 29. A plurality of connection adapters 32 corresponding to respective tubes 36 fit within a plurality of apertures 55 on opposing faces of the entrance chamber 11 and the exit chamber 12 for attachment of the tubes 36 in fluid communication with the entrance chamber 11 and exit chamber 12. In an alternate implementation for the testing of tubular prosthesis devices that are formed of materials that remain substantially nonporous under the pressure induced by the fatigue-testing system 60, the prosthesis devices may be directly attached to the connection adapters 32 to be placed in fluid communication with the entrance chamber 11 and the exit chamber 12.

A fluid flow pathway 38 is defined from the entrance chamber 11 to the exit chamber 12 passing through the central flow conduit 29 and also through the purality of tubes 36. When the prostheses 30 being tested are positioned within the tubes, the fluid flow path 38 may further include passage through the prostheses 30. In implementations in which tubular prostheses are attached directly to the adapters 32 between the entrance chamber 11 and the exit chamber 12 (rather than within prosthesis-housing structures), the fluid flow pathway is directly through the prostheses.

Testing pressures are created through a fluid drive member 10, which in the exemplary implementation shown is powered by a linear motor mounted inside a motor housing 9. The linear motor is composed of a primary 17a (i.e., the stator) and a secondary 17b that translates linearly within the primary. A circulation pump 37 has an outlet port in fluid communication with the entrance chamber 11. The circulation pump 37 provides controllable system flow for testing purposes and also helps ensure uniform temperature distribution. An emergency stop switch 14 is mounted on the base plate 8 and severs power to the system 60 in the case of an emergency.

The fatigue-testing device 20 may be pressurized, for example, by introducing pressurized air from an external air source 6, such as an air compressor or sealed pressurized volume. The system air pressure may be controlled via a pressure regulator 5. Alternatively, the system may be pressurized through the circulation pump 37 by controlling the flow rate and restricting outlet flow from a fluid exit valve 33. Before pressurization, a working fluid (not shown) is introduced into the entrance chamber 11 and/or the exit chamber 12, completely filling the device 20.

A heating source and fluid level safety switch are contained in a heat and circulation chamber 7. The heat and circulation chamber 7 also has inflow and outflow ports communicating with the exit chamber 12 and inlet port on the circulation pump 37, respectively. The heat and circulation chamber 7 is pressurized via a pressure regulator 5 and is completely sealed. A monitoring port allows the temperature inside the heat and circulation chamber 7 to be directly monitored.

The entrance and exit chambers 11, 12 along with the primary fluid system and flow path 38 are shown in FIG. 2. The plurality of prosthesis-containing housing tubes 36 are connected in fluid flow communication between the entrance and exit chambers 11, 12 as shown in FIG. 1. In exemplary embodiments, the inner diameters of the housing tubes 36 may preferably range from 1-50 mm. The plurality of housing tubes 36 are coupled in parallel between the entrance and exit chambers 11, 12 for simultaneous testing of prostheses 30.

The fluid flow pathway 38 within the main housing is illustrated by phantom lines in FIG. 2. A fluid drive member 10 is provided to pressurize and depressurize the system. The fluid drive member 10 is in direct fluid communication with the entrance chamber 11 and thereby with the exit chamber 12 and central flow conduit 29. Sample adapters 32, which allow the housing tubes 36 to be affixed to the fatigue-testing device 20 in a leak-free manner, are connected to the entrance chamber 11 and exit chamber 12. The sample adapters 32 can be adjusted, allowing the system to be easily configured for various prosthesis sizes. The entrance and exit chambers 11, 12 may also be configured to accommodate various sample quantities and geometries. A plurality of manifold plugs 31 in each of the entrance and exit chambers 11, 12 serve as fluid filling and air purge locations, as well as locations for monitoring ports.

It will be understood that during the primary or pressurization portion of a testing cycle, the fluid drive member 10 moves in a positive direction toward the entrance chamber 11, decreasing the system volume and creating system pressurization. During a secondary or depressurization portion of the test cycle the fluid drive member 10 moves in a negative direction away from the entrance chamber 11, increasing the system volume and depressurizing the system. These actions serve to pressurize and depressurize the housing tubes 36, applying the appropriate radial strain and/or pulse pressure to the prostheses. The central flow conduit 29 creates an alternate path for energy from the pressurization cycle such that the prostheses may be excited from both ends, which mitigates the formation of standing waves within the test prostheses. In this manner, the test prostheses are excited in a more natural and clinically relevant manner. The drive member 10 returns to its starting position and the process is repeated, cycling the fluid pressure on the prostheses. A single test cycle may consist of completion of both the first and secondary portions of the test cycle such that the prostheses complete a physiologically relevant expansion and contraction.

Monitoring transducers 52 can be inserted for continuous or periodic measurements through sample access valves 34 in the exit chamber 12. Typically, transducers 52 are used for temperature and pressure monitoring. However, it should be understood that a variety of sensing elements can be inserted in a similar fashion. The working fluid temperature is controlled via the fluid heater and a temperature transducer contained in the heat and circulation chamber 7 shown in FIG. 1. Upper and lower temperature bounds are set in the test software. At startup, the system 60 will begin to heat until the upper bound is reached. As the input temperature falls below the lower bound, the heater 7 may again be activated, thus maintaining a mean temperature within acceptable bounds. This mean temperature is typically set to 37° C. to simulate physiologic conditions. Other monitoring transducers 52 may be used to provide feedback to the computer 2 or control system 4 to monitor the status of any number of system variables to provide active control over the system 60, for example, to vary pump speed or control the stroke of the driver to provide consistent loading on the system 60.

Figure 3:
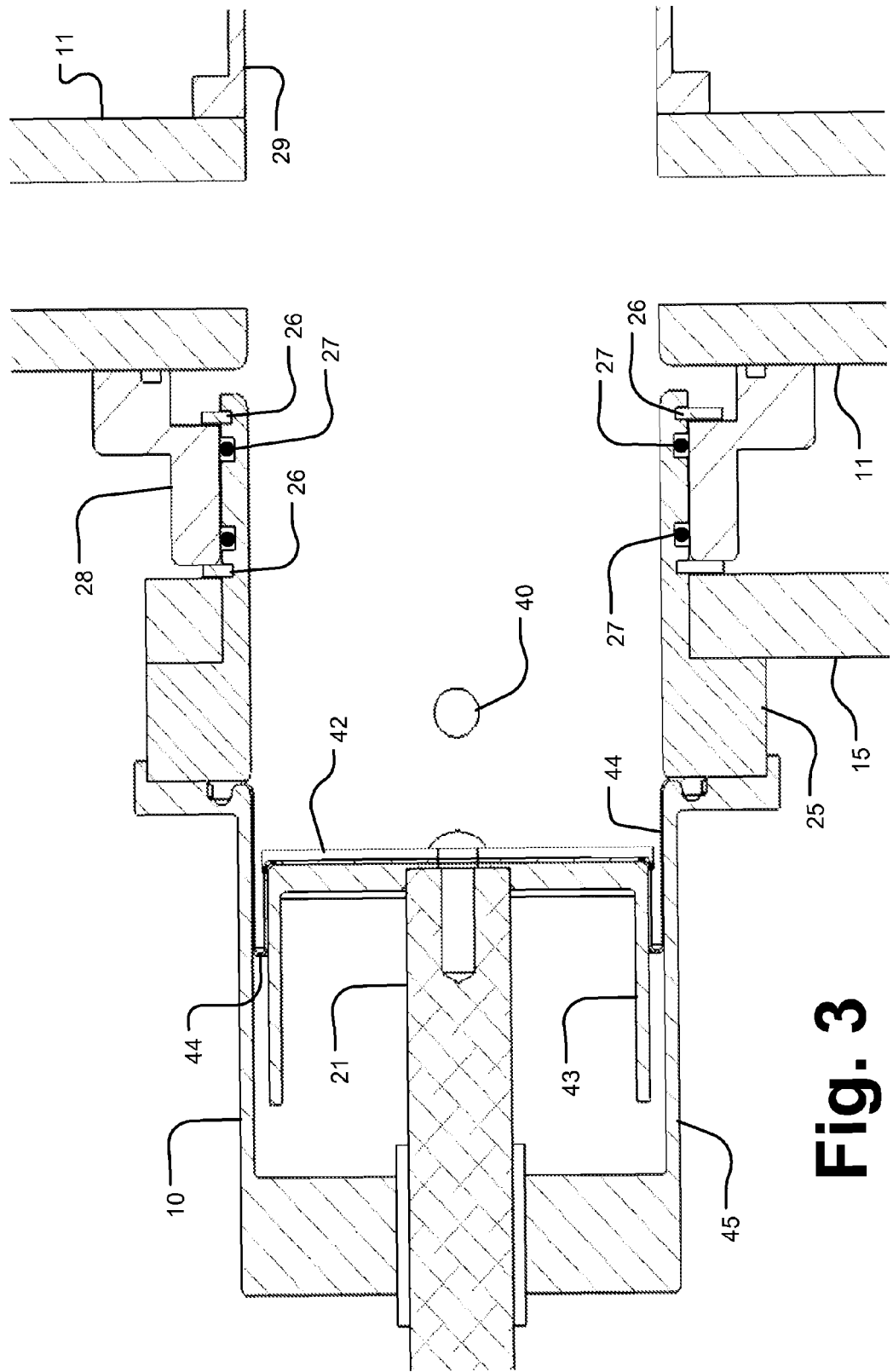
FIG. 3 is an enlarged partial cross-section view of the fatigue-testing apparatus of FIG. 1 detailing the fluid drive coupled with the rotational mechanism.

Turning to FIG. 3, the fluid drive member 10 is mounted to an entrance rotational support 25. Both, in turn, are affixed to the entrance support structure 15. The entrance rotational support 25 acts as a rotational bearing surface and allows the entrance chamber 11, which is affixed to the rotational member 28, to rotate freely about the central axis without the need for the drive member 10, linear motor 17, or motor housing 9 to rotate. The exit chamber 12 structure is supported by and configured to rotate about the central axis on exit chamber support wheels 24 shown in FIGS. 1 and 2. The entrance chamber 11 is connected to the rotational member 28 which maintains internal pressure through the entrance seals 27 and is held in place by the entrance retaining clips 26.

Fluid enters the fatigue testing device 20 through an inflow port 40 defined in the entrance rotational support 25 and exits the fatigue testing device 20 through the exit flow valve 33 contained in the exit chamber 12 as shown in FIG. 2. Alignment of the entrance and exit chambers 11, 12 is maintained through the central flow conduit 29. The central flow conduit 29 may be constructed of a single rigid section or composed of multiple telescoping sections (see FIG. 8) which allow for adjustment of the length of the housing tube 36.

In one implementation, the fluid drive member 10 has a flexible diaphragm drive system as illustrated in FIG. 3. The diaphragm 44 is housed inside a diaphragm cylinder 45. A rigid cap 42 clamps the diaphragm 44 to the moveable piston 43 mounted to a linear drive adapter 21 extending from the linear motor 17, while peripheral edges of the diaphragm 44 are sealed between the entrance rotational support 25 and a flange 56 about one end of the diaphragm cylinder 45. The diaphragm 44 is preferably a cap-like member constructed of a non-reactive and flexible thin rubber, polymeric or synthetic based material. The flexible diaphragm 44 is highly compliant with low resistance to axial deformation across its entire axial range of motion within the diaphragm cylinder 45 and entrance rotational support 25. In the implementation shown in FIG. 3, the diaphragm 44 may be considered a rolling bellows. However, alternative configurations of the diaphragm 44 may be employed so long as the configuration is capable of low friction and low resistance to deformation under the influence of the piston 43.

Many advantages of a low friction flexible diaphragm 44 or rolling bellows as opposed to a rigid metallic bellows or traditional piston and cylinder drive may be appreciated. The lateral surfaces of the diaphragm 44 evert as the piston 43 reciprocates within the diaphragm cylinder 45 and entrance rotational support 25. This eversion exerts very little resistance to piston 43 movement. These components are affixed to the entrance support structure 15 and maintain the pressure seal along the circumference of the diaphragm 44.

Figure 4:
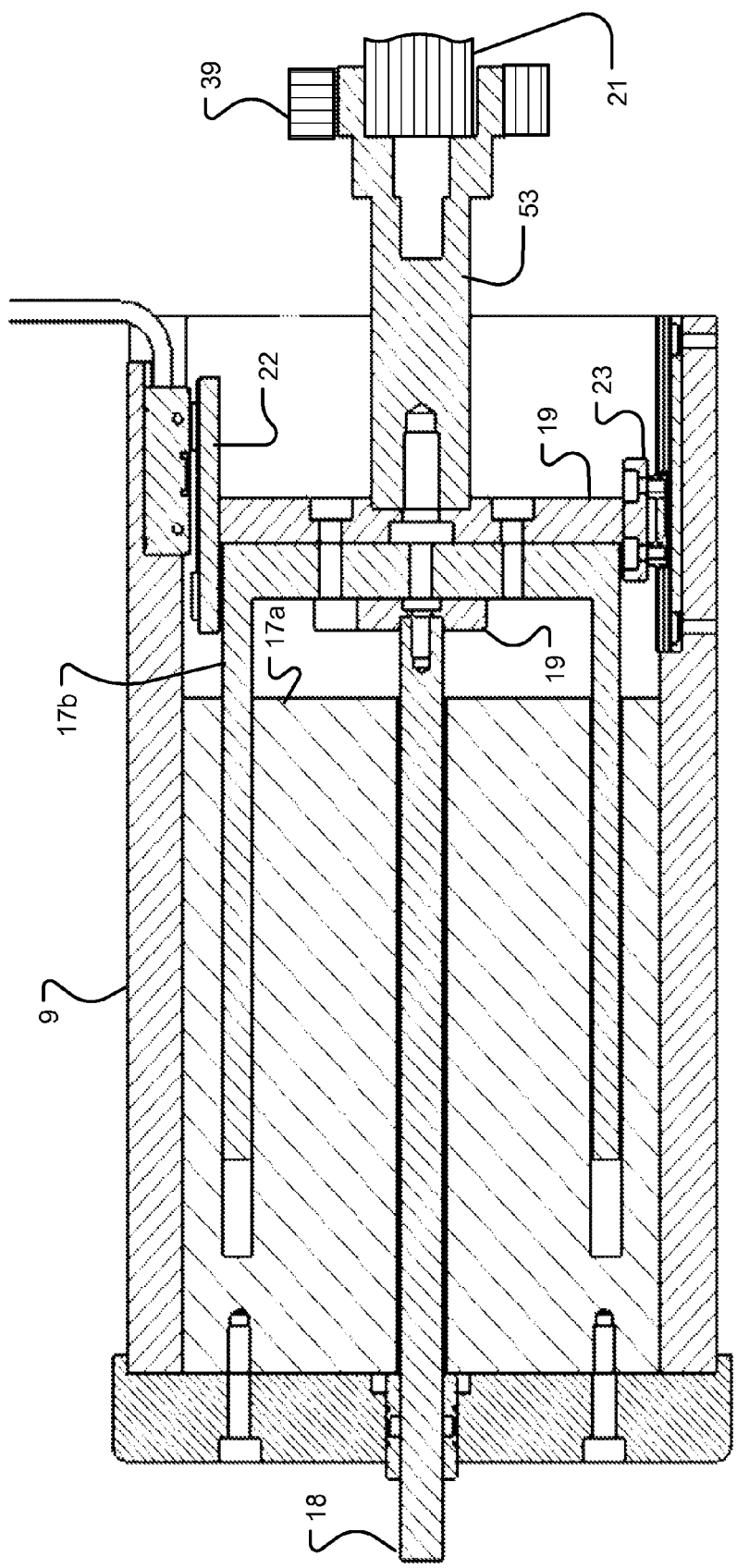
FIG. 4 is an enlarged partial cross-section view of the fatigue-testing apparatus of FIG. 1 showing the linear drive and support structure.

The motor support structure along with the linear motor 17 and alignment mechanisms are shown in detail in FIG. 4. The linear motor 17, which in some embodiments is electromagnetic, has a drive shaft 53 that is connected to the linear drive adapter 21, which may be configured to connect with linear drive shafts 53 of varying diameter. The linear drive adapter 21 is clamped onto the linear drive shaft 53 by the drive shaft clamp 39. Alignment is maintained through the motor alignment shaft 18 attached to a linear motor support structure 19 at one end and the housing 9 at the other. Rotation about the central axis may be prevented by the anti-rotation mechanism 23, consisting of a linear guide affixed to the motor support structure 19. Positional feedback may be provided by a linear encoder 22, which in one embodiment may be a non-contact, optical type. It should be understood that the linear motor 17 is not restricted to this particular configuration and various drive technologies may be employed with similar effect.

Figure 5:
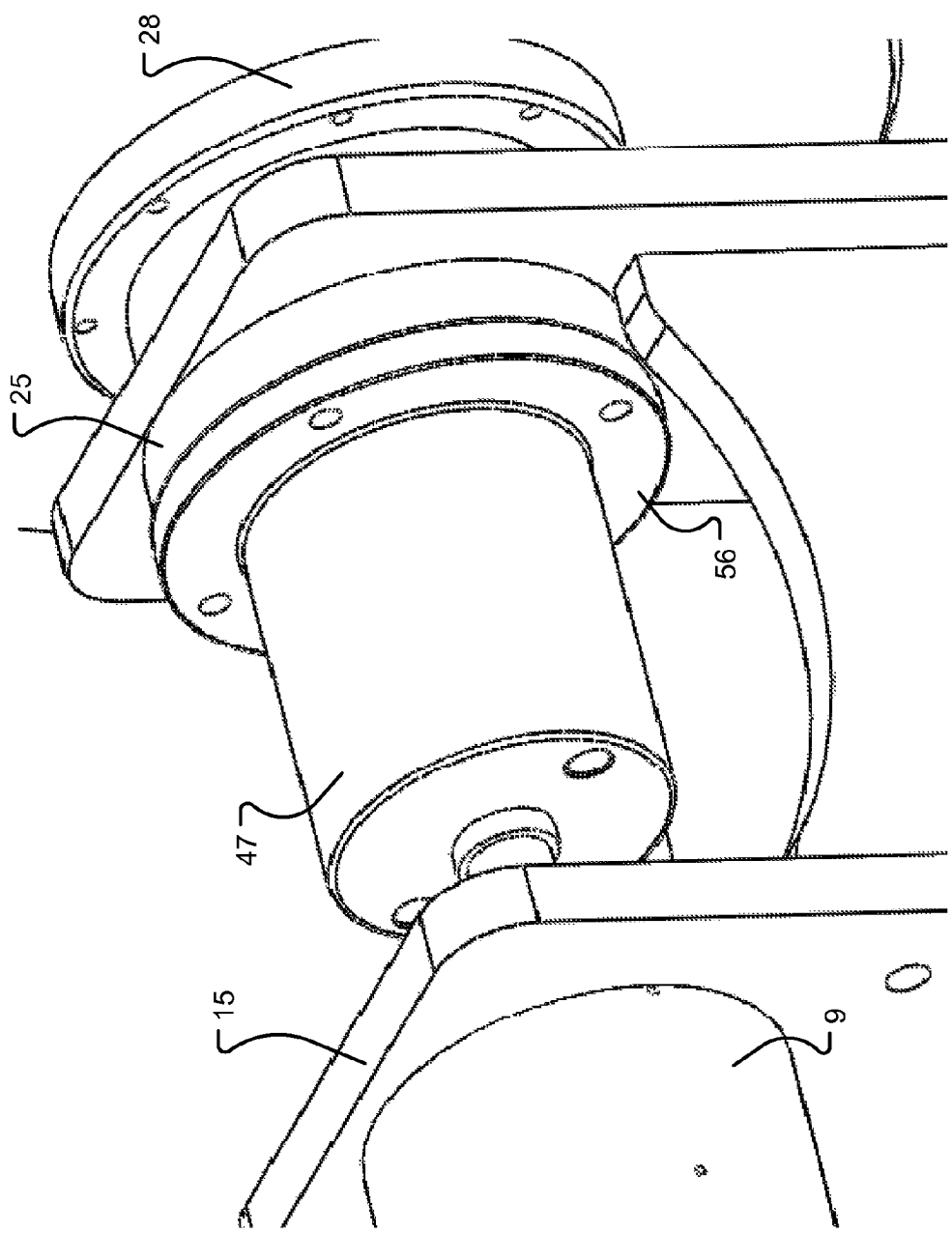
FIG. 5 is a partial isometric view of the fatigue-testing apparatus of FIG. 1 detailing the large fluid drive member.
Figure 6:
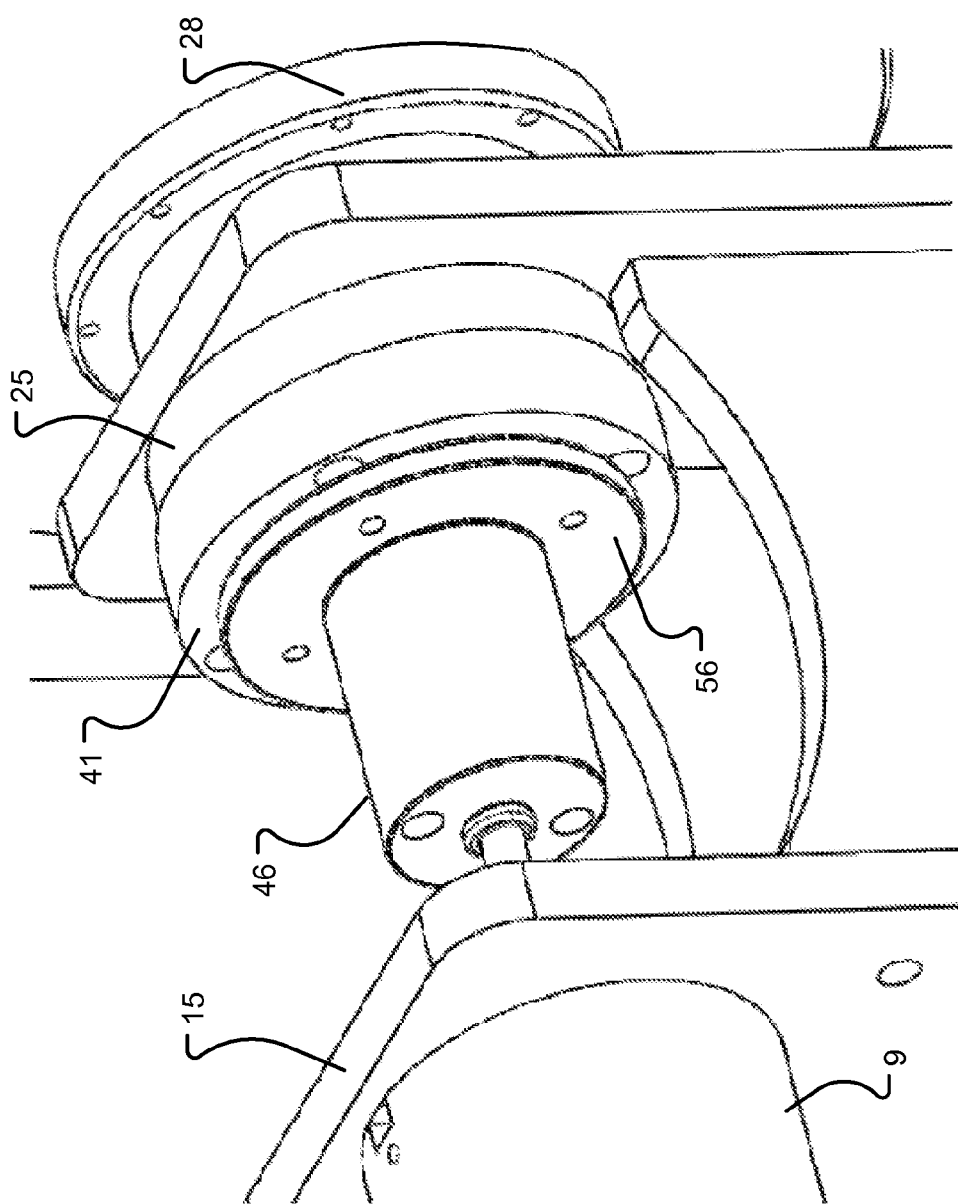
FIG. 6 is a partial perspective view of an alternate embodiment of a fluid-testing apparatus incorporating a small fluid drive member.

The fluid drive member 10 may be sized based on the volumetric requirements of the test by use of adaptor manifolds which are affixed to the main housing. Two possible drive member configurations are shown in FIGS. 5 and 6. FIG. 5 shows a large fluid drive member 47, typically used in conjunction with housing tubes 36 with a diameter of greater than 30 mm. FIG. 6 depicts an alternate embodiment of a small fluid drive member 46 coupled with an adapter manifold 41 to the entrance rotational support 25. This drive size is typically used in conjunction with housing tubes 36 with an internal diameter of 30 mm or less. It should be understood that the fluid drive member 10 is not restricted to these particular configurations and that any necessary volumetric displacement can be easily achieved.

Figure 7:
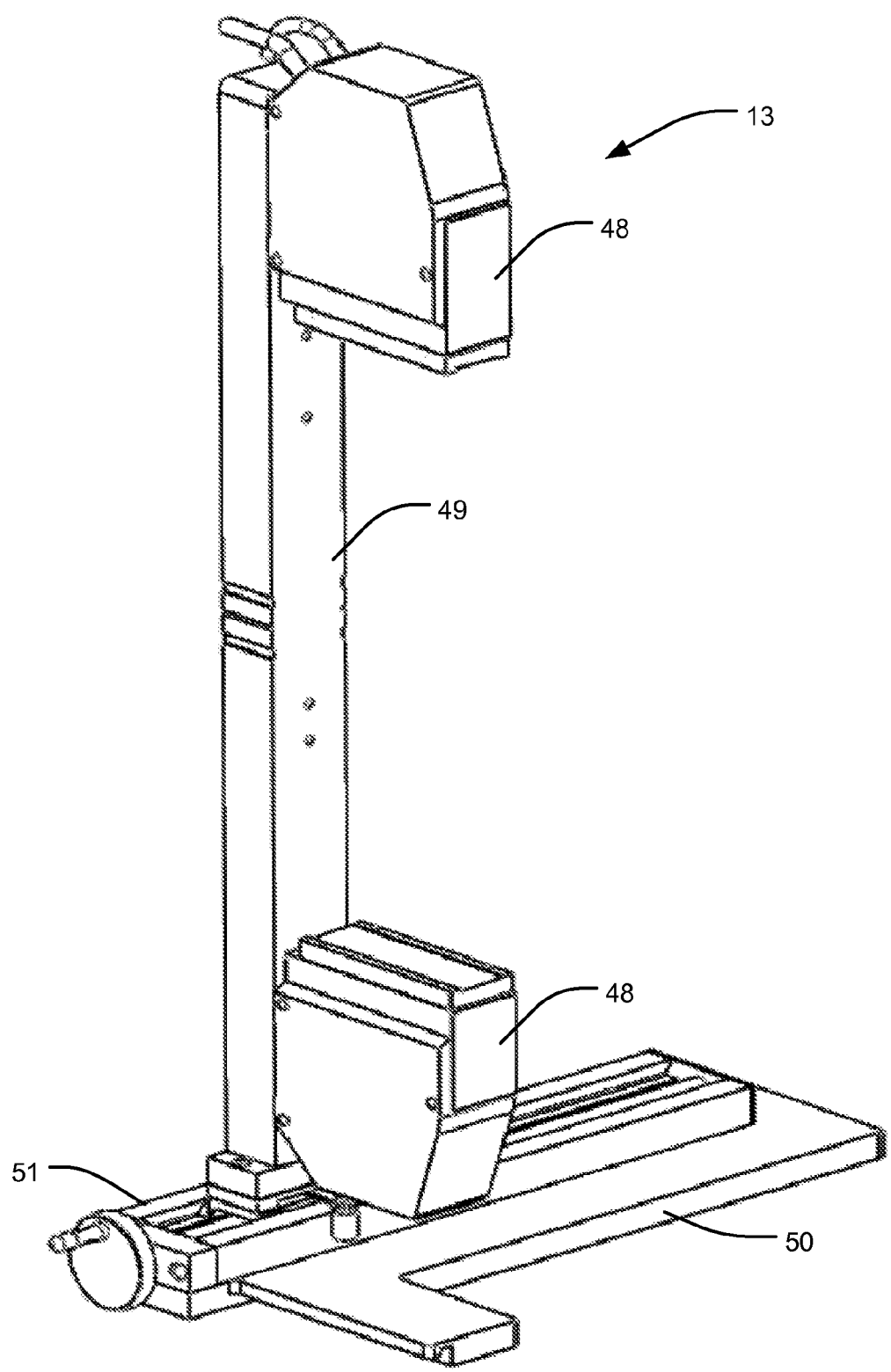
FIG. 7 is an isometric view of the optical micrometer measurement system of the fatigue-testing apparatus of FIG. 1.

The optical micrometer system 13 is illustrated in FIG. 7. The optical micrometer 48, which in one embodiment may be a high accuracy LED or laser type, is affixed to an optical micrometer support rail 49. The optical micrometer support rail 49 is joined to a precision slide 51. The precision slide 51 provides a structure for accurately and repeatedly positioning the optical micrometer 48. The precision slide 51 is affixed to the optical micrometer base 50. The optical micrometer base 50 is keyed to provide an accurate reference point when connected to an exit support structure reference datum 35 shown in FIG. 2. The optical micrometer 48 may thereby be used to inspect the prostheses 30 as they are placed under pressure in the fatigue-testing device 20. The optical micrometer 48 may be used to measure expansion and contraction sizes of the prostheses 30 along their lengths. The fatigue-testing device 20 may be rotated on the entrance and exit support structures 15, 16 during a test run to place each of the prostheses 30 being tested within the scanning range of the optical micrometer 48.

Figure 8:
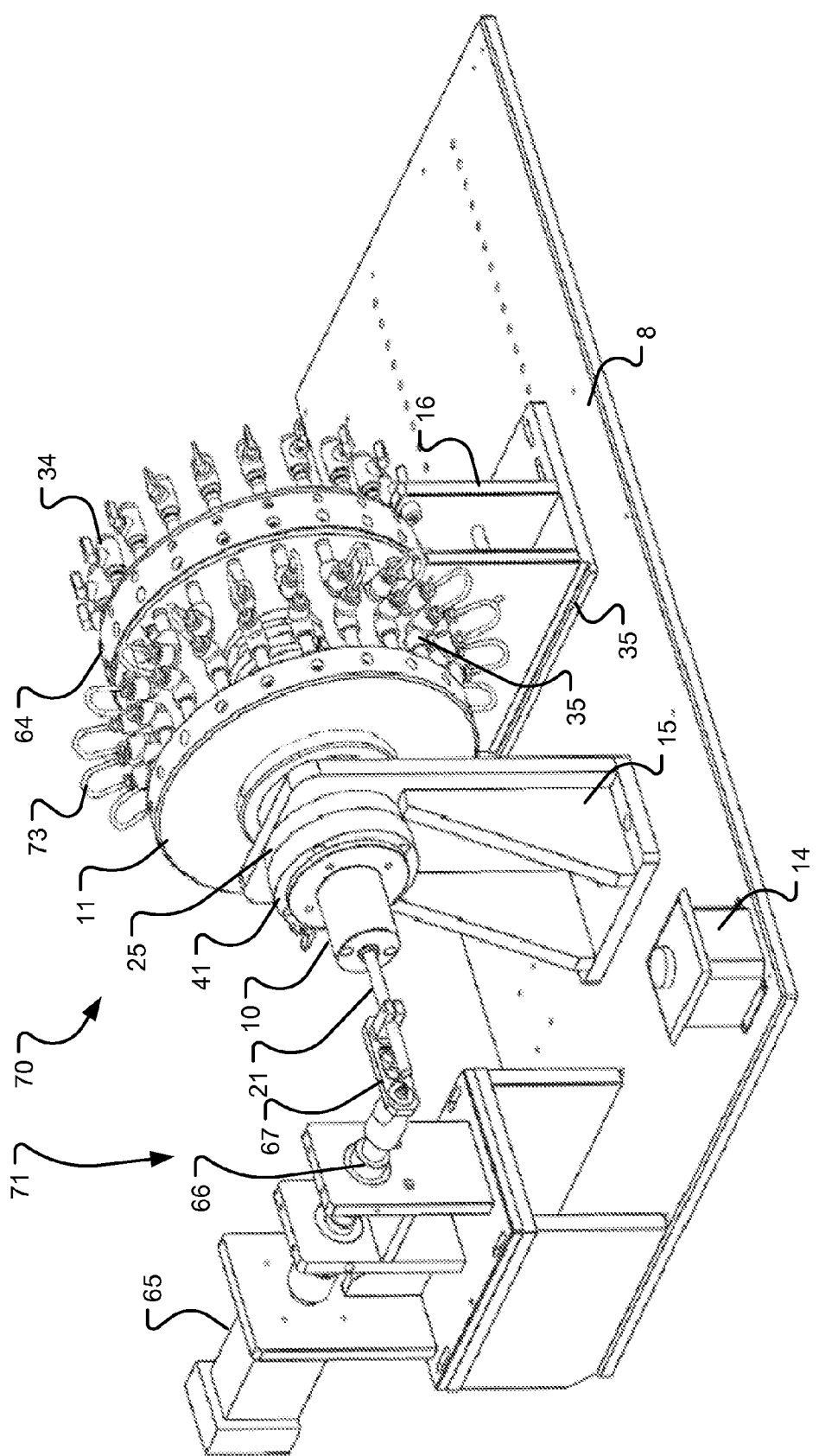
FIG. 8 is an isometric view illustrating an alternate embodiment of a fatigue-testing apparatus of a fatigue-testing system for prostheses.
Figure 9:
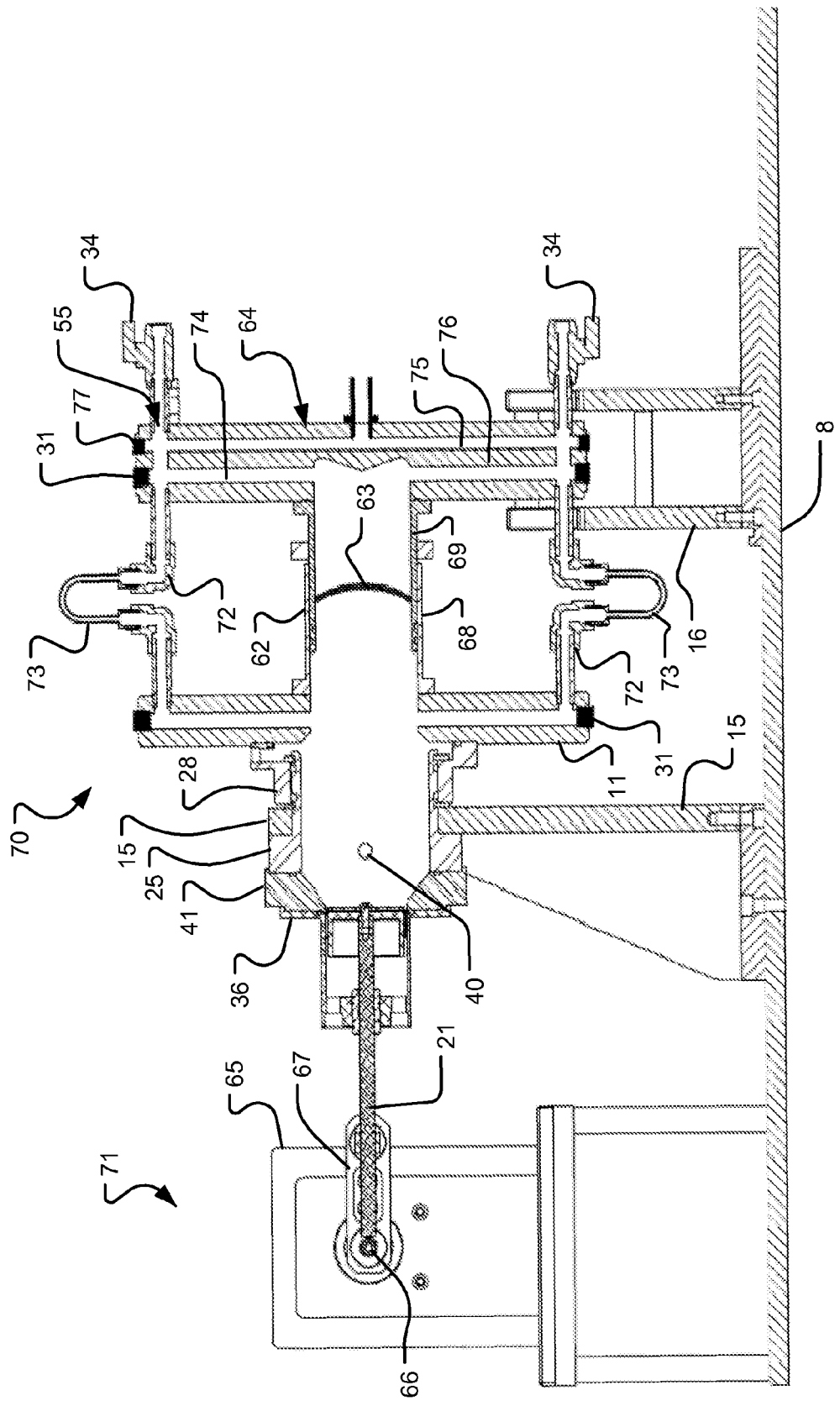
FIG. 9 is a cross-section view of the fatigue-testing apparatus of FIG. 1 showing a telescoping internal fluid chamber coupled with a rotary drive system.

An alternate embodiment fatigue-testing device 70 of a fatigue-testing system is shown in FIGS. 8 and 9 along with an alternate embodiment of a drive system 71. The fatigue testing device 70 is composed of a pressurizable fluid housing 61 formed as a disk-shaped manifold or entrance chamber 11 and a disk-shaped manifold or exit chamber 64 connected by a cylindrical, telescoping central flow conduit 62. The entrance and exit chambers 11, 64 are supported, respectively, by an entrance support structure 15 and an exit support structure 16. The support structures 15, 16 are affixed to a base plate 8.

A plurality of contoured tubes 73 (e.g., curved or bent, either regularly or irregularly), or other prosthesis-housing structures, or the prostheses themselves, extend between and are in fluid communication with the entrance chamber 11 and the exit chamber 64. The tubes 73 are arranged circumferentially around and spaced apart from the central flow conduit 62. A plurality of connection adapters 72 corresponding to respective contoured tubes 73 fit within a plurality of apertures 55 on opposing faces of the entrance chamber 11 and the exit chamber 64 for attachment of the tubes 73 in fluid communication with the entrance chamber 11 and exit chamber 64. In this exemplary embodiment, the tubes 73 are U-shaped in order to meet FDA requirements for testing of certain types of prostheses (e.g., coronary stents). In order to accommodate the U-shaped tubes 73, the connection adapters 72 may be formed as angled connectors with various bend angles. In an alternate implementation for the testing of tubular prosthesis devices that are formed of materials that remain substantially nonporous under the pressure induced by the fatigue-testing system, the prosthesis devices may be directly attached to the connection adapters 72 to be placed in fluid communication with the entrance chamber 11 and the exit chamber 64.

In the exemplary implementation of FIGS. 8 and 9, the central flow conduit 62 is telescopically formed of an entrance half 68 connected to the entrance chamber 11 and an exit half 69 connected to the exit chamber 64. As shown, the exit half 69 is configured with an outer diameter slightly smaller than the inner diameter of the entrance half 68, thereby allowing the exit half 69 to be received within the lumen of the entrance half 68. It should be apparent that in an alternate embodiment, the entrance half 68 could be sized and configured to be received within the exit half 69. The interface between the entrance half 68 and the exit half 69 forms a seal to prevent fluid leakage from the central flow conduit. The fluid seal may be provided by O-rings or other seal structures (not shown) disposed between the entrance half 68 and the exit half 69. The telescoping central flow conduit 62 is thus able to move axially during system setup, allowing different testing lengths of prostheses to be easily configured.

The alternate embodiment of the central flow conduit 62 shown in FIG. 9 has a compliance flow control membrane 63 disposed therein. The flow control membrane 63 separates the central flow conduit 62 into two portions, which allows energy to pass through the central flow conduit 62, but blocks the passage of fluid. This controls the circulatory flow of the system ensuring an even temperature distribution throughout the test system. It should be apparent that the flow control membrane 63 may be provided in either a telescoping or fixed-length central flow conduit design. As noted in FIG. 9, the flow control membrane 63 is preferably mounted within the inner portion of the telescoping central fluid conduit 62.

An alternate embodiment of the exit chamber 64 is also shown in FIG. 9. In this embodiment, the exit chamber 64 is provided with a primary manifold 74 that is in direct fluid communication with the central flow conduit 62 and a backchannel 75 that is separated from the primary manifold by a wall 76. The backchannel 75 is in fluid communication with the apertures 55 at which the sample adapters 72 and sample access valves 34. An additional set of manifold plugs 77 may be provided directly in line with the backchannel 75 adjacent to the manifold plugs 34 that provide access to the primary manifold 74 at each aperture 55. The backchannel 75 provides an additional flow channel in the exit chamber 64 to provide greater mixing of the fluid between the sample adapters 72 and access valves 34 to provide for more uniform temperature distribution. Again, it should be apparent that the backchannel 75 can be provided on either a telescoping or fixed-length pressurizable fluid housing design.

An alternate drive system 71 is also shown in FIGS. 8 and 9. In this exemplary embodiment, a shaft 66 of a rotary motor 65 (e.g., a servo or brushed motor) is coupled to a linkage system 67, in this case a crank and slider mechanism, that is further coupled to the linear drive adapter 21. In this manner, rotational motion from the rotary motor is translated to linear motion in order to drive the diaphragm inside the fluid drive member. Other types of motors with appropriate linkage systems may also be used to drive the fatigue-testing systems disclosed herein.

Embodiments of the fatigue-testing system disclosed herein are capable of simulating physiologic conditions on a prosthesis at an accelerated rate. This accelerated rate may be achieved through a combination of one or more of a variety of features. For example, the use of a low-inertia, flexible diaphragm drive system reduces burden on the motor allowing for more frequent cycling. The uniform pressure field provided across the sample housing by connecting the entrance and exit manifolds through the central flow conduit helps maintain consistent conditions across multiple prostheses simultaneously tested. Further, by providing an automated test interface capable of running without direct management, proper testing conditions and safety mechanisms are ensured over the course of the testing cycle.

The fatigue-testing system 60 is also flexible and capable of testing various prosthesis sizes and configurations. The design of the fluid housing with a central flow conduit allows for equal pressure assertion on prostheses from both ends while only needing a single driver on one side. Further, because the fatigue-testing device 20 is capable of rotation about a central axis by means of a stationary drive member and a rotary seal system, it allows for accurate external diameter measurements of the prostheses in the housing tubes at high frequency. An accurate reference feature for measurement of the prostheses by the optical measurement device 13 also aids in the efficiency of the system.

While the present invention has been described with reference to the particular embodiments set forth above, it will be understood that variations, such as those in construction, configuration, dimension, material selection and assembly, may be employed without departing from the spirit and scope of the present invention. All directional references (e.g., proximal, distal, upper, lower, upward, downward, left, entrance, exit, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A fatigue-testing system for prostheses comprising
a pressurizable fluid housing further comprising
an entry fluid chamber;
an exit fluid chamber; and
a plurality of pairs of connection adaptors mounted on respective facing sides of the entry fluid chamber and the exit fluid chamber, wherein the pairs of connection adaptors are configured to connect either directly with respective prostheses or with prosthesis-housing structures during fatigue testing cycles to place the prostheses or prosthesis-housing structures in fluid communication with the entry fluid chamber and the exit fluid chamber;
a drive motor; and
a flexible rolling bellows diaphragm connected with and driven axially by the drive motor that increases and decreases a pressure on a fluid in the pressurizable fluid housing.

2. The fatigue-testing system of claim 1 further comprising a central fluid conduit both structurally connecting the entry fluid chamber to the exit fluid chamber and providing pressure communication between the entry fluid chamber and the exit fluid chamber.

3. The fatigue-testing system of claim 2 further comprising a membrane within the central fluid conduit that fluidically separates the central fluid conduit into a first portion in fluid communication with the entry fluid chamber and a second portion in fluid communication with the exit fluid chamber.

4. The fatigue-testing system of claim 1 further comprising a plurality of tubes arranged between, connected to, and in fluid communication with the respective pairs of connection adapters, wherein the tubes are configured to house respective prostheses during fatigue testing cycles.

5. The fatigue-testing system of claim 1, wherein each of the connection adapters forms a contoured conduit.

6. The fatigue-testing system of claim 1, wherein the drive motor comprises a linear motor.

7. The fatigue-testing system of claim 1, wherein
the drive motor comprises a rotary motor; and
a linkage between the rotary motor and the flexible rolling bellows diaphragm.

8. The fatigue-testing system of claim 1, wherein a connection between the drive motor and the pressurizable fluid housing is configured to allow the pressurizable fluid housing to axially rotate with respect to the drive motor, which remains stationary.

9. The fatigue-testing system of claim 1, wherein a connection between the flexible rolling bellows diaphragm and the pressurizable fluid housing is configured to allow the pressurizable fluid housing to axially rotate with respect to the drive motor, which remains stationary.

10. The fatigue-testing system of claim 1 further comprising an optical micrometer system positioned to measure a dimension of a prosthesis mounted in the pressurizable fluid housing while the fatigue testing system is in operation.

11. The fatigue-testing system of claim 1, wherein the flexible rolling bellows diaphragm is in direct fluid communication with only the entry fluid chamber.

12. A fatigue-testing system for prostheses comprising
a pressurizable fluid housing further comprising
an entry fluid manifold for connecting with first ends of prostheses or with first ends of prosthesis-housing structures; and
an exit fluid manifold for connecting with second ends of prostheses or with second ends of prosthesis-housing structures;
a drive system that increases and decreases a pressure on a fluid in the pressurizable fluid housing; and
a connection structure between the drive system and the pressurizable fluid housing configured to allow the pressurizable fluid housing to axially rotate with respect to the drive system, which remains stationary.

13. The fatigue-testing system of claim 12 further comprising a collar mounted to the entry fluid manifold, wherein
the collar surrounds a port in the entry fluid manifold in fluid communication with the drive system;
the collar rotationally connects with a neck extending from the drive system that defines a fluid chamber in the drive system; and
the collar circumferentially, fluidically seals against the neck.

14. The fatigue-testing system of claim 13, wherein the collar is positioned about an outer surface of the neck.

15. The fatigue-testing system of claim 12 further comprising a central fluid conduit both structurally connecting the entry fluid manifold to the exit fluid manifold and providing pressure communication between the entry fluid chamber and the exit fluid chamber.

16. The fatigue-testing system of claim 15, wherein the central fluid conduit extends and contracts in length longitudinally.

17. The fatigue-testing system of claim 12, wherein the drive system comprises a drive motor and a flexible eversion diaphragm connected with and driven axially by the drive motor.

18. A method of testing fatigue in tubular prostheses comprising
mounting a tubular prosthesis between a first fluid manifold and a second fluid manifold, wherein the first fluid manifold and second fluid manifold are axially connected via a central fluid conduit to form a fluid housing;
filling the fluid housing with a working fluid whereby the working fills the tubular prosthesis between the first manifold and the second manifold and fills the central fluid conduit;
using a single driver to impart energy directly to the first manifold and the central fluid conduit to increase and decrease pressure on the working fluid in the fluid housing and mitigate a presence of standing waves in the tubular prosthesis.

19. The method of claim 18 further comprising driving a flexible eversion diaphragm to increase and decrease pressure within the fluid housing.

20. The method of claim 19 further comprising measuring a dimension of the tubular prosthesis while driving the flexible eversion diaphragm to increase and decrease the pressure.

21. The method of claim 19 further comprising rotating the fluid housing about an axis of the central fluid conduit while maintaining the single driver in a stationary position.

22. The method of claim 18, wherein the inserting operation further comprises increasing or decreasing a separation distance between the first manifold and the second fluid manifold by telescoping the central fluid conduit.

23. A fatigue-testing system for prostheses comprising
a pressurizable fluid housing further comprising
an entry fluid manifold for connecting with first ends of prostheses or with first ends of prosthesis-housing structures;
an exit fluid manifold for connecting with second ends of prostheses or with second ends of prosthesis-housing structures; and
a central fluid conduit that both structurally connects the entry fluid chamber to the exit fluid chamber and provides pressure communication between the entry fluid chamber and the exit fluid chamber; and
a drive system that increases and decreases a pressure on a fluid in the pressurizable fluid housing.

24. The fatigue-testing system for prostheses of claim 23, wherein the central fluid conduit telescopes to extend and contract in length longitudinally.

25. The fatigue-testing system of claim 23 further comprising plurality of pairs of connection adaptors mounted on respective facing sides of the entry fluid manifold and the exit fluid manifold, wherein the pairs of connection adaptors are configured to connect either directly with respective prostheses or with prosthesis-housing structures during fatigue testing cycles to place the prostheses or prosthesis-housing structures in fluid communication with the entry fluid manifold and the exit fluid manifold.

26. The fatigue-testing system of claim 23, wherein the drive system further comprises
a linear drive motor; and
a flexible eversion diaphragm connected with and driven axially by the drive motor that increases and decreases the pressure on the fluid in the pressurizable fluid housing.

27. The fatigue-testing system of claim 23 further comprising a membrane within the central fluid conduit that fluidically separates the central fluid conduit into a first portion in fluid communication with the entry fluid manifold and a second portion in fluid communication with the exit fluid manifold.

28. The fatigue-testing system of claim 24, wherein the telescoping central fluid conduit comprises
an inner conduit connected to either the entry fluid chamber or the exit fluid manifold; and
an outer conduit connected to whichever of the entry fluid chamber or the exit fluid manifold is not connected to the inner conduit; wherein
the inner conduit is configured to slide within the outer conduit and an outer wall of the inner conduit creates a fluid-tight seal with an inner wall of the outer conduit.

29. The fatigue-testing system of claim 23, wherein the drive system is connected only to the entry fluid manifold.

30. A fatigue-testing system for prostheses comprising
a pressurizable fluid housing further comprising
an entry fluid manifold for connecting with first ends of prostheses or with first ends of prosthesis-housing structures;
an exit fluid manifold for connecting with second ends of prostheses or with second ends of prosthesis-housing structures; and
a central fluid conduit both structurally connecting the entry fluid manifold to the exit fluid manifold and providing pressure communication between the entry fluid manifold and the exit fluid manifold; wherein
the exit fluid manifold further comprises
a primary manifold in direct fluid communication with the central fluid conduit; and
a backchannel separated from the primary manifold and in indirect fluid communication with the central fluid conduit via the primary manifold; and
a drive system that increases and decreases a pressure on a fluid in the pressurizable fluid housing.

31. The fatigue-testing system of claim 30, wherein the drive system further comprises
a linear drive motor; and
a flexible eversion diaphragm connected with and driven axially by the drive motor that increases and decreases the pressure on the fluid in the pressurizable fluid housing.

32. The fatigue-testing system of claim 30 further comprising plurality of pairs of connection adaptors mounted on respective facing sides of the entry fluid manifold and the exit fluid manifold, wherein the pairs of connection adaptors are configured to connect either directly with respective prostheses or with prosthesis-housing structures during fatigue testing cycles to place the prostheses or prosthesis-housing structures in fluid communication with the entry fluid manifold and the exit fluid manifold.

33. The fatigue-testing system of claim 30 further comprising a membrane within the central fluid conduit that fluidically separates the central fluid conduit into a first portion in fluid communication with the entry fluid manifold and a second portion in fluid communication with the exit fluid manifold.

* * * * *